(12) United States Patent
Baskis

(10) Patent No.: US 7,144,507 B2
(45) Date of Patent: Dec. 5, 2006

(54) DRY CYCLE ANAEROBIC DIGESTER

(76) Inventor: Paul Baskis, 339 S. Century Blvd., Rantoul, IL (US) 61866

( * ) Notice: Subject to any disclaimer, the term of this patent is extended or adjusted under 35 U.S.C. 154(b) by 0 days.

(21) Appl. No.: 10/735,516

(22) Filed: Dec. 11, 2003

(65) Prior Publication Data

US 2004/0154983 A1    Aug. 12, 2004

Related U.S. Application Data

(60) Provisional application No. 60/432,083, filed on Dec. 11, 2002.

(51) Int. Cl.
*C02F 3/28* (2006.01)

(52) U.S. Cl. ............... 210/603; 210/615; 210/252; 435/262.5

(58) Field of Classification Search ........... 210/603, 210/605, 615–617, 630, 252, 259; 435/262, 435/262.5; 71/9, 10, 23
See application file for complete search history.

(56) References Cited

U.S. PATENT DOCUMENTS

| | | | | |
|---|---|---|---|---|
| 1,434,520 A | * | 11/1922 | Ball | 210/251 |
| 2,823,106 A | * | 2/1958 | Pierson | 71/9 |
| 2,867,521 A | * | 1/1959 | Jeffreys | 71/8 |
| 4,655,925 A | * | 4/1987 | Tabata et al. | 210/605 |
| 4,818,405 A | * | 4/1989 | Vroom et al. | 210/603 |
| 4,917,805 A | * | 4/1990 | Reid | 210/605 |
| 5,076,928 A | * | 12/1991 | Ballnus | 210/605 |
| 5,647,986 A | * | 7/1997 | Nawathe et al. | 210/608 |
| 5,863,433 A | * | 1/1999 | Behrends | 210/602 |
| 5,989,428 A | * | 11/1999 | Goronszy | 210/605 |
| 6,065,224 A | * | 5/2000 | Eigner | 34/322 |
| 6,096,214 A | * | 8/2000 | Ripley | 210/603 |
| 6,299,774 B1 | * | 10/2001 | Ainsworth et al. | 210/603 |
| 6,325,935 B1 | * | 12/2001 | Hojsgaard | 210/609 |
| 2001/0047960 A1 | * | 12/2001 | Sato et al. | 210/616 |
| 2004/0063193 A1 | * | 4/2004 | Suominen | 435/262 |
| 2006/0011757 A1 | * | 1/2006 | Palm | 241/27 |

FOREIGN PATENT DOCUMENTS

JP    7-308688    * 11/1995
JP    8-224590    * 9/1996

* cited by examiner

*Primary Examiner*—Fred G. Prince
(74) *Attorney, Agent, or Firm*—Hunton & Williams LLP

(57) ABSTRACT

The present invention provides a digester for handling waste or contaminated materials. A process and an apparatus for processing are disclosed. A Dry Cycle Anaerobic Digester (DCAD) uses tanks to perform aerobic and anaerobic digestion to eliminate the waste, while producing little or no sludge.

16 Claims, 6 Drawing Sheets

DRY CYCLE ANAEROBIC DIGESTER

CROSS-REFERENCE TO RELATED APPLICATIONS

The application claims the benefit of provisional application 60/432,083, filed Dec. 11, 2002.

BACKGROUND OF THE INVENTION

The invention relates to the processing of waste materials or contaminated materials.

SUMMARY OF THE INVENTION

The present invention provides a digester for handling waste or contaminated materials. A process and an apparatus for processing are disclosed. A Dry Cycle Anaerobic Digester (DCAD) uses tanks to perform aerobic and anaerobic digestion to eliminate the waste, while producing little or no sludge.

The present invention is versatile, dependable and can be tuned for variable operation. Optimum operation could be maximum reduction and degradation of a waste stream with only carbon dioxide, soluble nutrients and water emissions; alternatively the maximum production of methane gas may be the most desirable operating environment. The system design allows for the selection of the microbial environment that provides the best operating conditions, as determined by the user. The system is designed to mimic Mother Nature and the Earths natural systems that deal with nutrient cycling. The system consists of alternating aerobic and anaerobic digestion cycles.

Maximizing time intervals for substrate introduction increases the aerobic time cycle and encourages high rates of digestion. This introduces a large amount of carbon dioxide into the microbial environment. Substantial heat production occurs during this phase and the high temperature during this stage of operation aids in the degradation or digestion of the material through simple hydrolysis. Enzymes from a wide array of microorganisms also play an important part in this digestion stage. Soluble organics and carbon dioxide rich water travel to the second digester and undergo anaerobic digestion where considerable methane production occurs.

Decreasing the time between wetting intervals increases the methane production and is the beginning of the anaerobic cycle. This cycle has lower efficiency for digesting a wide variety of material. The methanogens utilize fatty acids and in the process co-metabolize carbon dioxide into methane. However, total organic processing capability would decrease. This can lead to a larger size unit for the same nutrient load. However, a sufficiently oversized reactor can be a significant methane producer that will produce good quality gas for use in a boiler, gas turbine engine or modified diesel generator.

Tuning the DCAD unit is simple. The primary decision is whether the farm operation requires the removal of the largest amount of waste possible by the DCAD or the production of methane gas. If the primary goal is to digest the farm waste organic material into carbon dioxide and water then you want your unit tuned to provide maximum aerobic cycle times. This means that introduction of solid waste material my be possible providing that water introduction is timed at wide intervals, resulting in a reactor that is running with a high oxidation rate. This system operation will degrade organic farm waste very efficiently and is similar to the green hay phenomenon that has burned down many barns. Unlike the barn example, when the digester pile has reached a predetermined temperature the pile is wetted and the digester swings into anaerobic digestion mode. Bacteria that were dormant rapidly swing into action and utilize the fatty acid production that has built up from the rapidly degrading organic pile.

This action is very similar to the rain event and drying cycles that occur everyday on Earth. Life is dynamic and has evolved to deal with change. Change is ubiquitous in the environment. Bacteria that are active after a wetting event are utilizing simple sugars and water-soluble proteins and carboxylic acids. While utilizing these compounds for life support they produce an exogenous material that works on the more complex structure in the organic farm waste. As the pile begins to dry the environment becomes micro aerophylic and bacteria begin to utilize some of the early degradation compounds. These bacteria also emit exogenous material that act as enzymes and begin to further degrade the reacting pile. The temperature of the pile begins to elevate and the pile loses more water. Now the environment is shifting to aerobic and the result is rapidly rising temperature and very efficient biological degradation. These microbes are releasing their exogenous compounds and further adding to the degradation of the most complex proteins, cellulose and lignin. At this point the bacteria population has reached the senescence phase of their population growth and would begin to decline naturally, leading to a lower level of activity associated with the stagnant environment. In this system a wetting event occurs at a selected parameter and the whole cycle begins over. Each cycle and interval in the cycle produces some desired effect with respect to the digesting pile and the cycle will continue as long as water and an energy supply is available.

DETAILED DESCRIPTION OF THE INVENTION

The process is a multiple environment biological process. The natural model of microbial succession is paramount in the operation of the process. In the natural environment, there are rain events and drying events. This causes a natural biological succession where different microbes that are favored by the particular environmental conditions at that time grow and proliferate rapidly. As these microbes begin to flourish and their populations climb they begin to ameliorate their immediate environment, changing the ecological conditions to favor another group of microbes that in turn grow and ameliorate their environment to produce condition favoring the next group of microbes. This produces in a cyclical environment that favors a large diversity of microbes able to perform different tasks in the degradation of organic material. Therefore, all organic material is eventually degraded into carbon dioxide, methane, and water.

Figure 1:
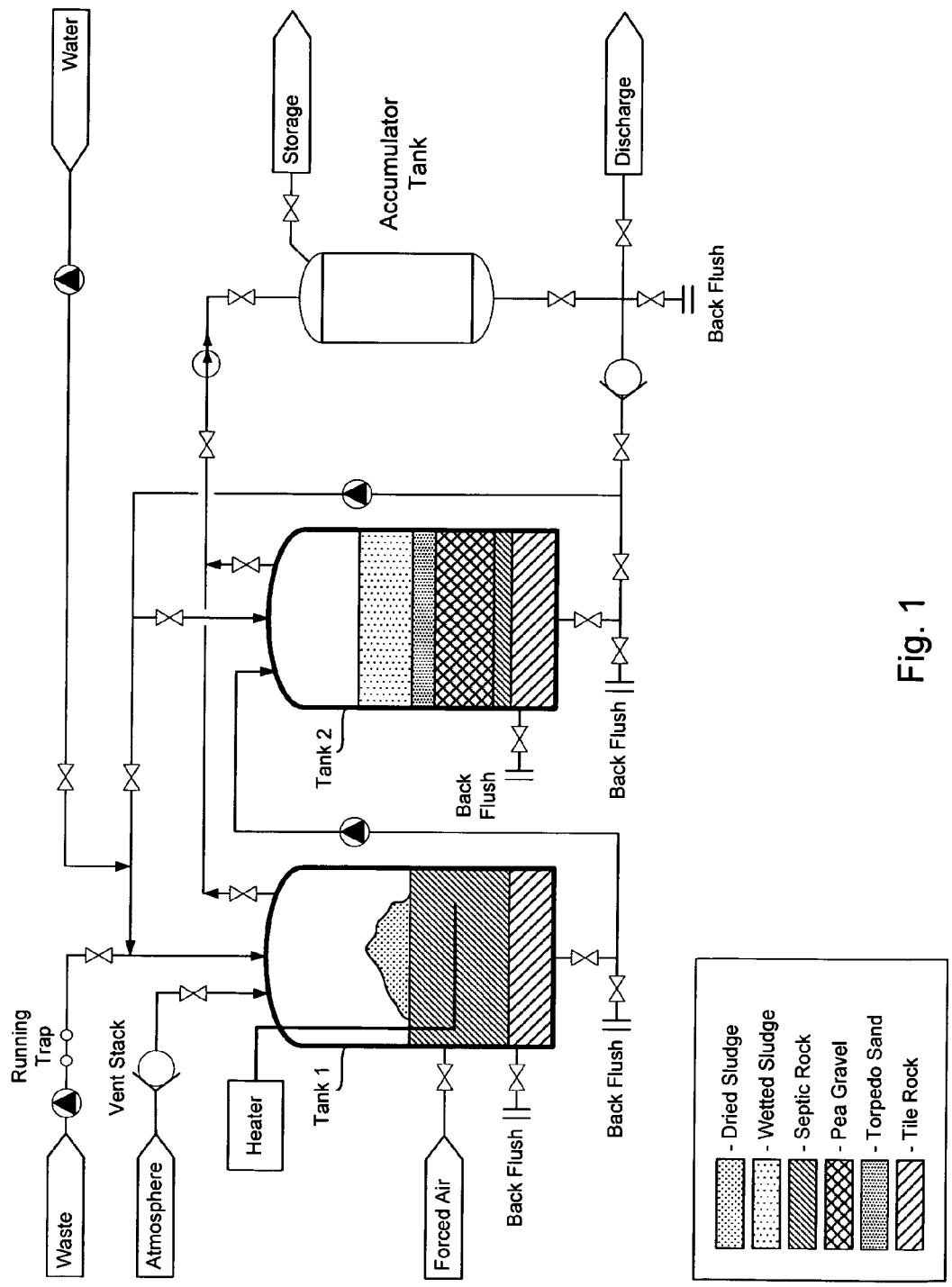
FIG. 1 is a schematic drawing of a digester system according to an embodiment of the invention.
Figure 2A:
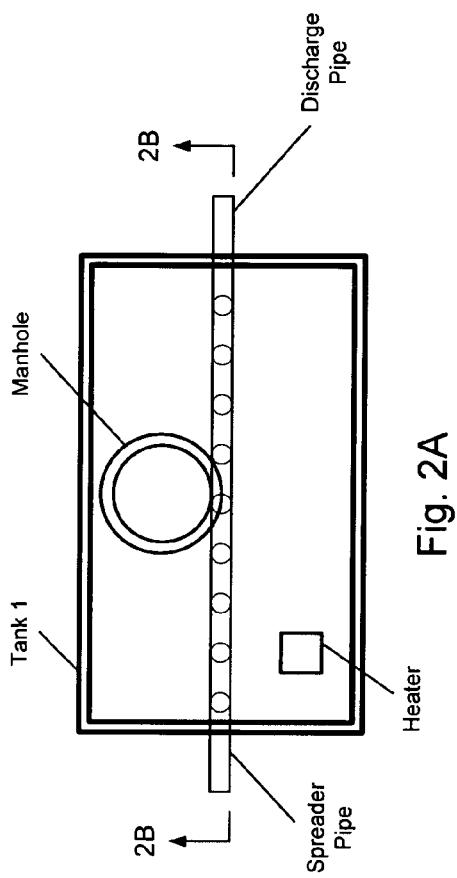
FIG. 2A is a top view of a digester tank that may be used in embodiments of the invention.
Figure 2B:
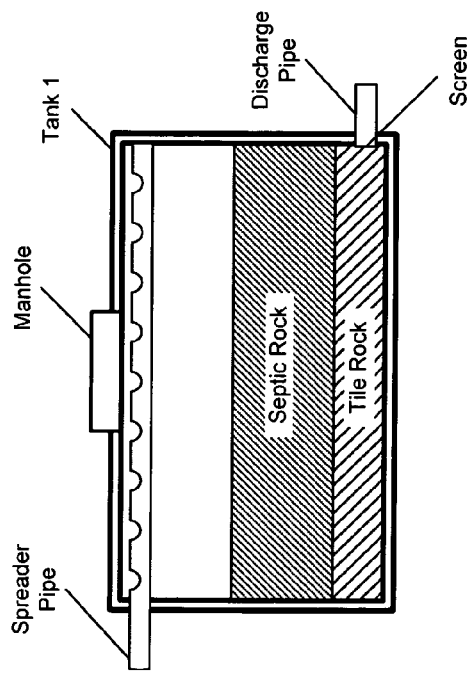
FIG. 2B is a section view of the digester tank in FIG. 2A.
Figure 3A:
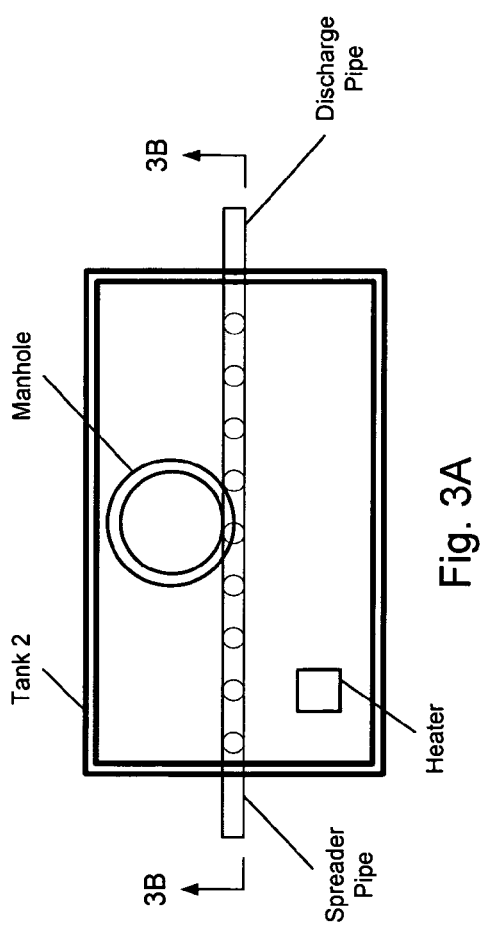
FIG. 3A is a top view of a digester tank that may be used in embodiments of the invention.
Figure 3B:
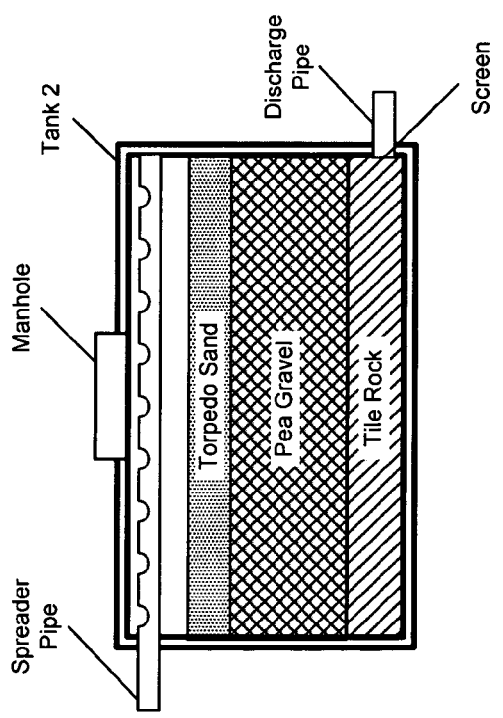
FIG. 3B is a section view of the digester tank in FIG. 3A.
Figure 4:
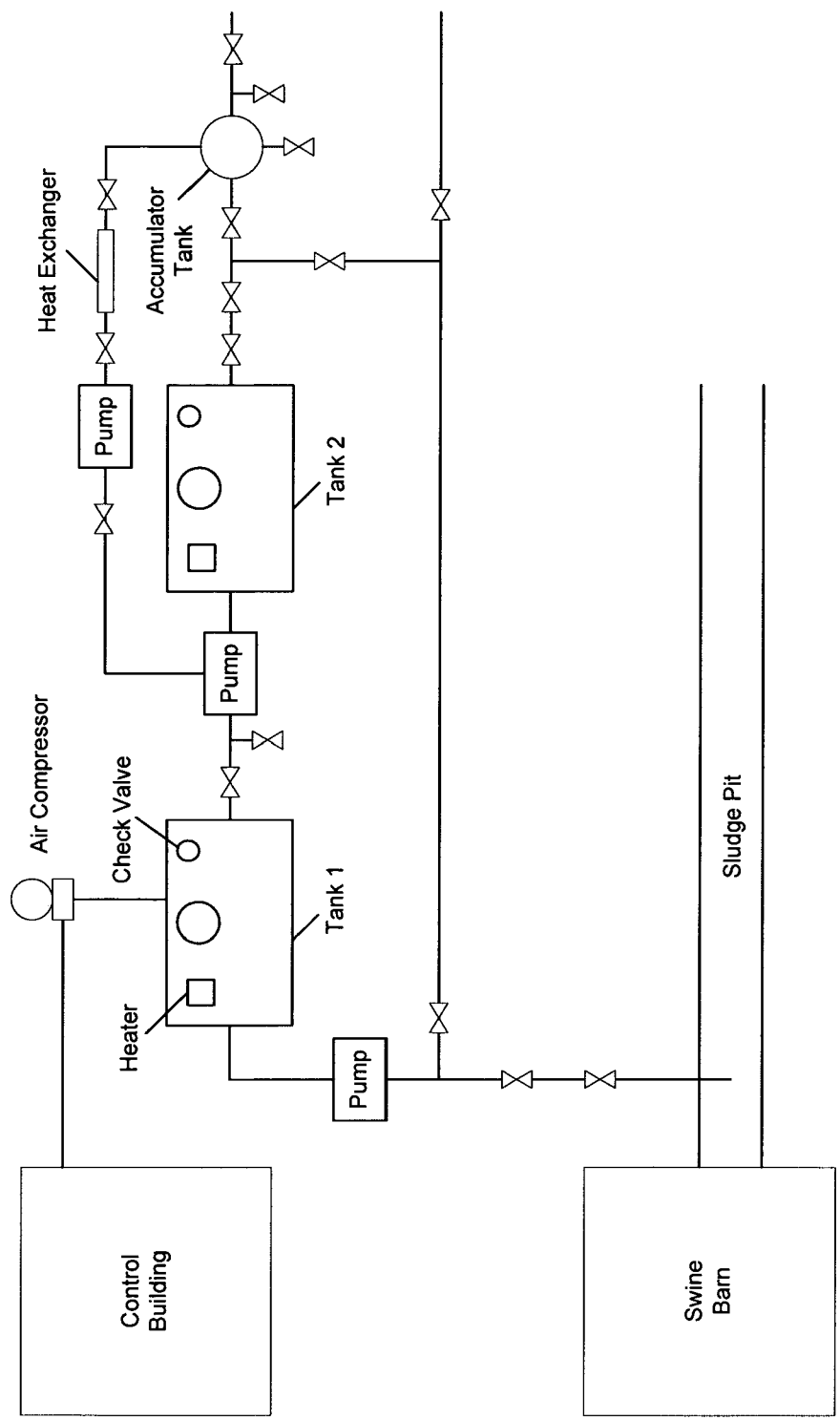
FIG. 4 is a schematic drawing of a digester system according to an embodiment of the invention.
Figure 5:
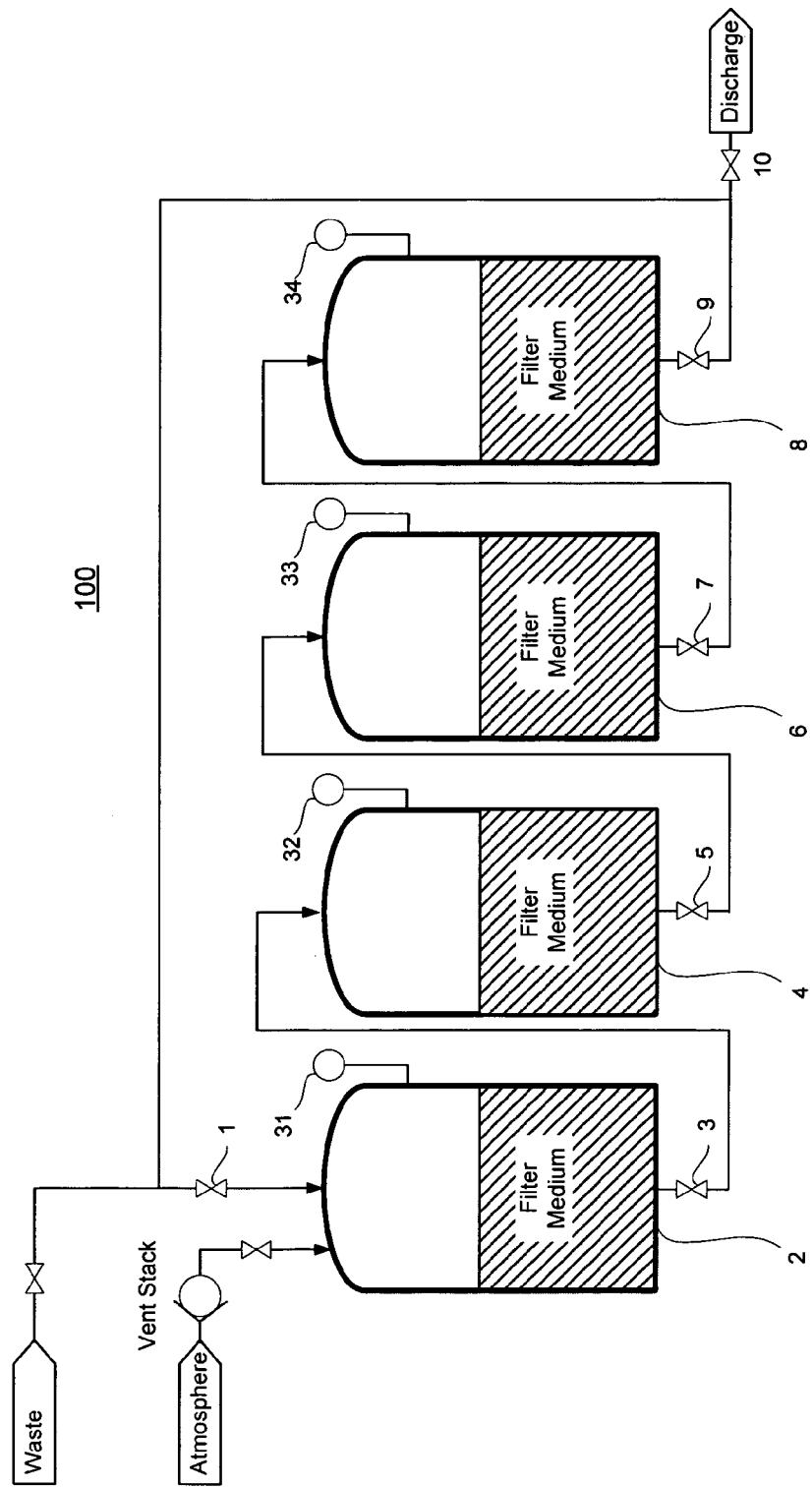
FIG. 5 is a schematic drawing of a digester system according to an embodiment of the invention.
Figure 6:
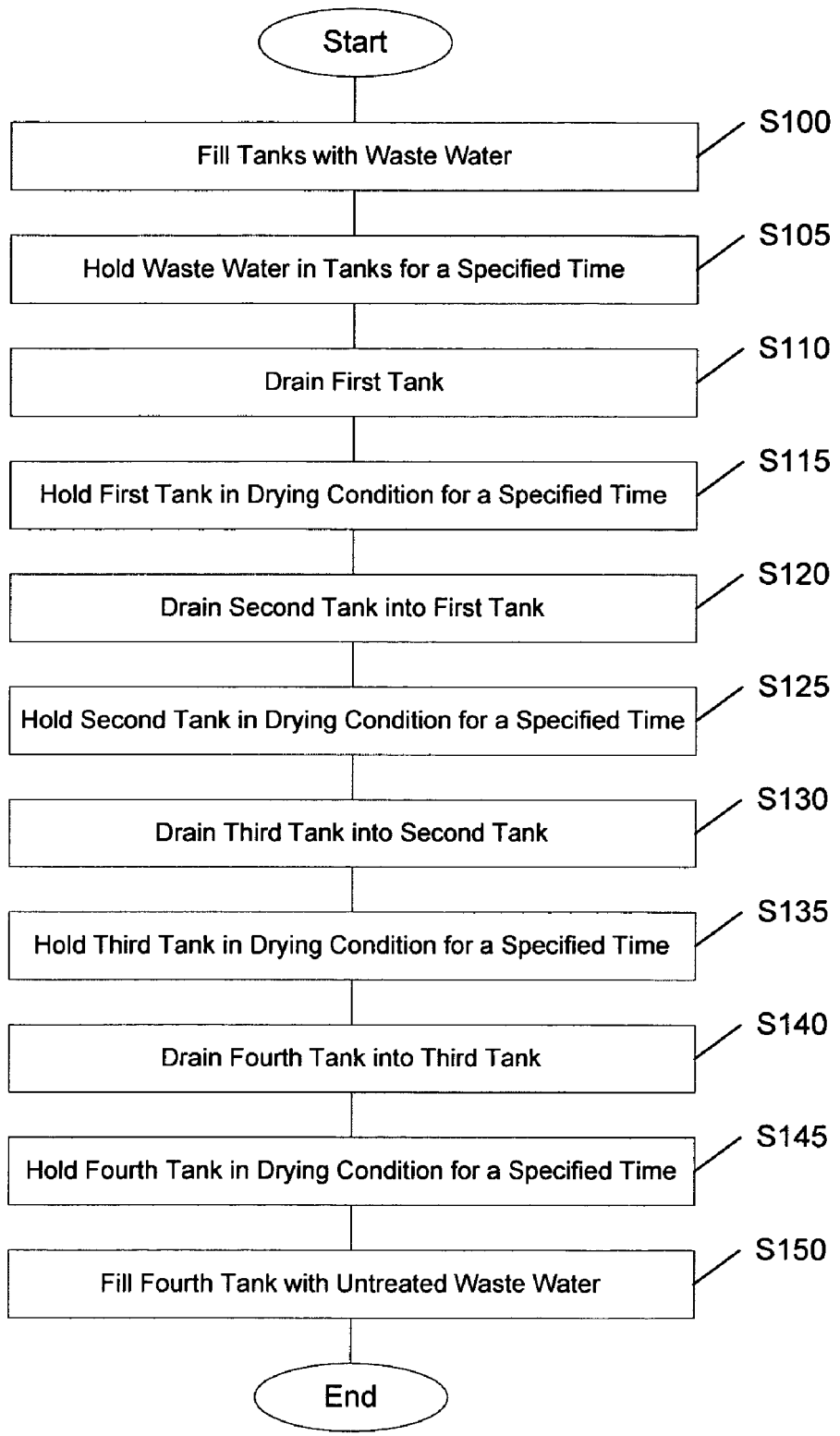
FIG. 6 is a flow diagram of a method of digesting materials according to an embodiment of the invention.

With reference to FIGS. 5 and 6, the procedure for system (100) start up is that all of the tanks (2, 4, 6 & 8) are filled with the waste water at S100. This is done by closing valve (9) and allowing tank (8) to fill until it reaches the point where the level indicator (34) is actuated. This stops the inflow into tank (8) by closing valve (7) and begins to fill tank (6). This tank (6) again fills until the level indicator (33) is actuated and closes valve (5) stopping the flow into tank (6) and begins to fill tank (4). Tank (4) fills until it reaches the point where the level indicator (32) is actuated and closes valve (3) causing tank (2) to begin to fill. Tank (2) again fills until it reaches the point where the level indicator (31) is actuated and close valve (1).

At this point the system is full and held like this for a specified time at S105 as determined by the operator to begin the bacterial growth phase. Once the allotted time has passed tank (8) is emptied at S110 and held in this drying condition for a specified time as selected by the operator at S115. When the allotted time has passed valve (7) is opened by the time and tank (6) is drained into tank (8) at S120 until the level indicator in tank (8) is actuated and closes valve (7). Now tank (8) is again full and tank (6) is empty. Tank (6) is held in this drying condition for an allotted amount of time as determined by the operator at S125. After the specified time has passed the timer actuates valve (5) and begins to fill tank (6) and empty tank (4) at S130. Tank (4) is again held empty for a specified time for its drying event at S135 and then the timer will actuate valve (3) and begin to fill tank (4) again and empty tank (2) at S140. Tank (2) is held empty for a specified time as determined by the operator at S145. When the allotted time has passed the timer will actuate valve (1) and allow untreated grey water from the fat floatation system to flow into tank (2) at S150. This system of sequencing the filling and emptying of the tanks (2, 4, 6, & 8) continue indefinitely. The times for the drying events are dependent upon the water analysis of the water leaving the system at valve (10). Valve 10 is normally open during operation and only closed if purging the tanks becomes necessary. Once the appropriate time has been determined the system will continue in this cycle for as long as desired.

One final purge system has been added to this process for the purpose of cleaning the tanks if necessary. This system consists of a pump and valves. These valves are manually set by the operator to provide for flushing the tanks (2, 4, 6, & 8) by pump if and when needed. They can be energized in any sequence that will allow for back flushing the required tank and then switching the valve so the pump can then empty the tank this will allow the removal of mineral sediment and the transfer of this sediment to a lagoon or marsh land area. These valves can also be switched so that they allow the water from the bottom of any one of the tanks (2, 4, 6, & 8) by pump and then pumped to the top of any one of the tanks (2, 4, 6,& 8). This will allow for the water to be trickled through the tank that is desired and increase the microbial activity and contact with the surface area of the filter medium.

This system has 3 optional systems. The first option is that atmospheric air can be drawn in through a check valve if found to be required under normal activity. This would only be needed if the flow of air into the system was not sufficiently supplied by the vent stack or that the fumes coming out of the system were not desirable. Normally any vent air should have no odor or minimal odor associated with it due to the aerobic activity in the digester system. However, if this does become a problem the vent stack would be closed and the air would be drawn in through the check valve and leave through another valve and travel to the lagoon and be exited the system under water to filter out unwanted odor. This normally will not be a problem, but is included in the design for situations that may require this to be done.

The last optional system is one to provide the microbial community nutrients if they require it. Some material such as fat may require the addition of small amounts of limiting nutrient to provide for the effective degradation of the fat. If this becomes a problem, a tank, and pump will be added to supply liquid nutrients to the process system.

The invention claimed is:

1. A method of processing waste materials in a treatment system comprising a plurality of reactor tanks, the method comprising:
    filling each of the plurality of tanks with waste material from a waste material source, the waste material comprising organic material and microbes capable of digesting at least a portion of the organic material;
    holding the waste material in the tanks for a time interval sufficient to allow the microbes to digest at least a portion of the organic material in a bacterial growth phase; and
    draining liquid from a first one of the plurality of tanks to allow at least a portion of the microbes and undigested organic material to dry within the first one of the plurality of tanks.

2. A method according to claim 1 further comprising:
    refilling the first one of the plurality of tanks with waste material from the waste material source.

3. A method according to claim 1 further comprising:
    transferring waste material from a second one of the plurality of tanks to the first one of the plurality of tanks.

4. A method according to claim 3 further comprising:
    allowing at least a portion of the microbes and undigested organic material to dry within the second one of the plurality of tanks.

5. A method according to claim 4 further comprising:
    refilling the second one of the plurality of tanks with waste material from the waste material source.

6. A method according to claim 4 further comprising:
    transferring waste material from a third one of the plurality of tanks to the second one of the plurality of tanks.

7. A method according to claim 6 further comprising:
    allowing at least a portion of the microbes and undigested organic material to dry within the third one of the plurality of tanks.

8. A method according to claim 7 further comprising:
    refilling the third one of the plurality of tanks with waste material from the waste material source.

9. A method according to claim 7 further comprising:
    transferring waste material from a fourth one of the plurality of tanks to the third one of the plurality of tanks.

10. A method according to claim 9 further comprising:
    allowing at least a portion of the microbes and undigested organic material to dry within the fourth one of the plurality of tanks.

11. A method according to claim 10 further comprising:
    refilling the fourth one of the plurality of tanks with waste material from the waste material source.

12. A method according to claim 10 further comprising:
transferring waste material from a fourth one of the plurality of tanks to the third one of the plurality of tanks.

13. A process for digesting materials comprising:

providing a reaction container having a medium disposed therein;

receiving a stream of materials to be treated into the reaction container, the stream of materials including organic waste material and microbes capable of digesting at least a portion of the organic material;

holding the materials in the reaction container for a time interval sufficient to allow the microbes to digest at least a portion of the organic material in a bacterial growth phase;

draining liquid from the reaction container to allow at least a portion of the microbes and undigested organic material to dry within the reaction container; and receiving an additional stream of materials to be treated into the reaction chamber with said at least a portion of the microbes and undigested organic material, the additional stream of materials including additional organic waste material and microbes, wherein the digestion of organic material by the microbes produces methane and the process further comprises selectively removing methane from the reaction container.

14. The process for digesting materials of claim 13, wherein the stream of materials to be treated comprises substantially organic agricultural waste.

15. A process for digesting materials according to claim 13 further comprising:

after draining liquid from the reaction container, maintaining dry conditions within the reaction container for a predetermined time interval.

16. A process for digesting materials according to claim 13 further comprising:

repeating the actions of holding the materials in the reaction container, draining liquid from the reaction container, and receiving an additional stream of materials to be treated into the reaction chamber.

* * * * *